US00RE38688E

(19) United States
(12) Reissued Patent
Friesen et al.

(10) Patent Number: US RE38,688 E
(45) **Date of Reissued Patent: *Jan. 18, 2005**

(54) SHEET-LIKE DIAGNOSTIC DEVICE

(75) Inventors: Heinz-Jürgen Friesen, Dagobertshausen (DE); Gerd Grenner, Binningen (CH); Hans-Erwin Pauly, Dautphetal (DE); Helmut Kohl, Wetter (DE); Klaus Habenstein, Wetter (DE); Joseph Stärk, Ebsdorfergrund (DE)

(73) Assignee: Dade Behring Marburg GmbH, Marburg (DE)

( * ) Notice: This patent is subject to a terminal disclaimer.

(21) Appl. No.: 09/820,974

(22) Filed: Mar. 30, 2001

Related U.S. Patent Documents

Reissue of:
(64) Patent No.: 4,861,711
Issued: Aug. 29, 1989
Appl. No.: 06/808,563
Filed: Dec. 13, 1985

U.S. Applications:
(63) Continuation of application No. 08/544,579, filed on Oct. 18, 1995, now Pat. No. Re. 37,437.

(30) Foreign Application Priority Data

Dec. 15, 1984 (DE) ..... 3445816

(51) Int. Cl.[7] ..... G01N 33/543

(52) U.S. Cl. ..... 436/518; 422/55; 422/56; 422/57; 422/58; 435/7.92; 435/7.93; 435/7.95; 435/287.1; 435/287.2; 435/805; 435/806; 435/969; 435/970; 435/971; 435/974; 436/65; 436/164; 436/169; 436/514; 436/528; 436/541; 436/810; 436/814; 436/818; 436/510

(58) Field of Search ..... 422/55–58; 435/292, 435/293, 295, 805, 806, 969, 970, 971, 974, 287.1, 287.2; 416/514, 518, 528, 541, 810, 814, 818, 510, 164, 169, 65

(56) References Cited

U.S. PATENT DOCUMENTS

| | | | | |
|---|---|---|---|---|
| 3,620,677 A | | 11/1971 | Morison | |
| 3,847,553 A | * | 11/1974 | Verbeck | 422/56 |

(List continued on next page.)

FOREIGN PATENT DOCUMENTS

| | | | | |
|---|---|---|---|---|
| CA | 1185882 | | 4/1985 | |
| DE | 23 32 760 | | 3/1982 | |
| DE | 30 43 608 | | 6/1982 | |
| DE | 33 29 728 | | 2/1984 | |
| DE | 33 29 628 | | 3/1984 | |
| EP | 0 046 004 | * | 2/1982 | 422/56 |
| EP | 0 052 328 | | 5/1982 | |
| EP | 0 088 636 A2 | | 9/1983 | |
| EP | 0 097 952 A2 | | 1/1984 | |

(List continued on next page.)

OTHER PUBLICATIONS

European Patent Application of Fuji Photo Film Co., Ltd., Publication No. A2 0 097 952, dated Jan. 11, 1984.*

(List continued on next page.)

*Primary Examiner*—Christopher L. Chin
(74) *Attorney, Agent, or Firm*—Finnegan, Henderson, Farabow, Garrett & Dunner, L.L.P.

(57) ABSTRACT

A solid diagnostic device for the quantitative determination of substances of biological affinity in biological fluids is described. A process is also described in which the biological fluid is brought into contact with a specific functional sector of the device, the fluid migrates through several functional sectors situated beside one another and containing suitable reagent components, and one or more substances of biological affinity are detected in such functional sectors which contain, for each substance to be detected, at least one combination partner of biological affinity, attached to a solid phase.

14 Claims, 2 Drawing Sheets

U.S. PATENT DOCUMENTS

| | | | | | |
|---|---|---|---|---|---|
| 4,094,647 | A | * | 6/1978 | Deutsch et al. | 436/810 |
| 4,258,001 | A | | 3/1981 | Pierce et al. | |
| 4,361,537 | A | * | 11/1982 | Deutsch et al. | 422/56 |
| 4,366,241 | A | * | 12/1982 | Tom et al. | 435/7.91 |
| 4,446,232 | A | * | 5/1984 | Liotta | 435/7.93 |
| 4,447,526 | A | * | 5/1984 | Rupchock et al. | 422/56 |
| 4,459,358 | A | * | 7/1984 | Berke | 436/170 |
| 4,472,498 | A | * | 9/1984 | Masuda et al. | 435/7.7 |
| 4,496,654 | A | | 1/1985 | Katz et al. | |
| 4,496,658 | A | * | 1/1985 | Kondo et al. | 436/510 |
| 4,517,288 | A | * | 5/1985 | Giegel et al. | 436/514 |
| 4,594,327 | A | * | 6/1986 | Zuk | 436/514 |
| 4,631,174 | A | * | 12/1986 | Kondo | 422/56 |
| 4,690,907 | A | | 9/1987 | Hibino et al. | |
| 4,740,468 | A | * | 4/1988 | Weng et al. | 435/805 |
| 4,756,828 | A | | 7/1988 | Litman et al. | |
| 4,757,004 | A | | 7/1988 | Houts et al. | |
| 4,861,711 | A | | 8/1989 | Friesen et al. | |
| 5,073,484 | A | | 12/1991 | Swanson et al. | |
| 5,120,643 | A | | 6/1992 | Ching et al. | |

FOREIGN PATENT DOCUMENTS

| | | | |
|---|---|---|---|
| EP | 0 100 619 | * | 2/1984 |
| EP | 0 186 799 | | 7/1986 |
| FR | 2 191 734 | | 1/1974 |
| GB | 1 440 464 | | 6/1976 |
| GB | 2126224 | | 3/1984 |
| JP | 48-5925 | | 1/1973 |
| JP | 53-47894 | | 4/1978 |
| JP | 55-90859 | | 7/1980 |
| JP | 57-113363 | | 7/1982 |
| JP | 58-76763 | | 5/1983 |
| JP | 58-179357 | | 10/1983 |
| JP | 61-145459 | | 7/1986 |

OTHER PUBLICATIONS

West German Offenlegungsschrift No. 33 29 628, dated Feb. 23, 1984.*

West German Offenlegungsschrift No. 30 43 608, dated Jun. 24, 1982.*

West German Patentschrift No. 23 32 760, issued Mar. 4, 1982.*

Hawkes et al., "A Dot–Immunobinding Assay for Monoclonal and Other Antibodies", *Analytical Biochemistry*, 119(1):142–147 (1982).

Hashimoto, Thin Layer Cfromatography, pp. 1–4 (Hirokwawa Shoten 1962, Tokyo) (with English translation).

Maruzen, *Experimental Chemistry Course 2 Fundamental Techniques II*, pp. 215–216 (Japan Chemistry Society ed. 1956, Tokyo) (with English translation).

Maruzen, *Experimental Chemistry Guidebook*, pp. 218–219 (Japan Chemistry Society ed. 1984, Tokyo) (with English translation).

Nakamura, "General Principles of Immunoassays," *Immunochemical Assays and Biosensor Technology for the 1990's*, pp. 3–7 (Robert Nakamura ed., American Society for Microbiology 1992, Washington, D.C.).

Nanzando, *Thin Layer Chromatography*, pp. 40–41 (Masayuki Ishikawa et al. ed. 1963, Tokyo) (with English translation).

Suzuki, "Tests in Thin Layer Chromatography," *Hirokawa Chemical Series No. 3*, pp. 18–20, (Hirokawa Shoten 1964, Tokyo) (with English translation).

Towbin et al., "Electrophoretic Transfer of Proteins from Polyacrylamide Gels to Nitrocellulose Sheets: Procedure and Some Applications," *Proc. Natl. Aca. Sci.*, 76(9):4350–4354 (1979).

Van Raamsdonk et al., "Detection of Antigens and Antibodies by an Immuno–Perozidase Method Applied on Thin Longitudinal Sections of SDS–Polyacrylamide Gels," *J. Immunological Methods*, 17:337–348 (1977).

Zuk et al., "Enzyme Immunochromatography—A Quantative Immunoassay Requiring No Instrumentation," *Clin. Chem.*, 31(7):1144–1150 (1985).

* cited by examiner

EXAMPLES OF TEST ASSEMBLIES WITH SAMPLE OR WITH PREVIOUS DILUTION OF SAMPLE IN THE FORM OF MOBILE PHASE

SHEET-LIKE DIAGNOSTIC DEVICE

Matter enclosed in heavy brackets [ ] appears in the original patent but forms no part of this reissue specification; matter printed in italics indicates the additions made by reissue.

*Notice: More than one reissue application has been filed for the reissue of Pat. No. 4,861,711. The reissue applications are application number 08/544,579, filed Oct. 18, 1995, now U.S. Reissue Pat. No. RE37,437 E, and 09/820, 974 (the present application), a continuation of 08/544,579.*

The invention relates to a solid diagnostic device which comprises several functional sectors and is used for the detection and quantitative determination of substances or analytes in biological fluids. The invention also relates to a process using this device in which, after the device has come into contact with the fluid, the analytes react with specific combination partners having biological affinity and are detected by means of labelling reagents.

In methods of diagnosis, the ability to identify and estimate specific compounds has made it possible to monitor the administration of medicaments, the quantification of physiologically active compounds or secondary products thereof and the diagnosis of infections. In this respect, the immunoassay methods (RIA, ELSIA and the agglutination test) are of particular importance. The specific combination reactions utilized in the tests are not limited to immunological interactions, such as antigen-antibody or hapten-antibody interactions, but also utilize interactions having biological affinity, such as lectin-sugar or active compound-receptor.

Although the existing tests are sensitive and specific, they do not constitute convenient application forms, because of the long duration of the test (in most cases several hours or even days) and the frequent test steps, such as immune reaction, washing steps and enzymatic reaction. The long test times are not compatible with use in emergency methods of diagnosis.

Integrated dry chemical test elements, such as are described in the present invention, simplify the performance of the tests and shorten the test times.

No sheet-like test element, in which all the components of the immune reaction of a heterogeneous immunoassay using solid phase detection, and the functional performance and the "bound-free" separation, are integrated has been described so far.

Whereas in the test strip assembly the immune reaction steps and the separation of bound and free phases are operated in the heterogeneous test by directed streams of liquid, in test element assemblies operating by means of thin layers laminated over one another (film technology), processes controlled by diffusion and directed by the concentration gradient are possible driving forces. A fluorescence labelling is used in German Offenlegungsschrift No. 3,329, 728 (Japanese Patent No. P144,341/82) and EP A No. 0,097,952 (Japanese Patent No. 114,359/82). The labelling has a low molecular weight and hence promotes processes controlled by diffusion. However, the test has to be carried out at an elevated temperature. In the first of these two cases both the free phase and also the bound phase are evaluated. In film technology the absorption of solvent is effected either by hydrating sellable components or by filling capillary cavities. In the case of assemblies having layers laminated over one another only the top layer and the bottom layer are accessible to detection without major difficulties.

After the reaction steps have taken place it is difficult to react reagents with components in intermediately placed layers. In the test strip assembly having zones situated one behind another, such as is used in the present invention, in principle each zone is readily accessible, both from above and also from below, for a determination and also for the addition of reagents which may perhaps be required.

The invention relates to a sheet-like diagnostic device which contains all the reagent components and which contains not only all the components required for the functional sequence, but also the functional sequences themselves in an integrated form, and by means of which it is possible to detect an analyte having properties of biological affinity, in such a way that a solution of the analyte is brought into contact with a functional region of the device designed for this purpose, and the analyte as detected via a signal-producing system in a single functional region, a solid phase zone.

A second analyte, or further analytes, as constituents of the same solution can be detected at the same time by means of the device, if these analytes possess properties of biological affinity different from the first analyte. They are also detected in the same manner as the first analyte in a single functional region, a solid phase zone appropriate for them. The functional regions for the detection of the second or further analytes are situated on the sheet-like device in front of or behind the functional region for the detection of the first analyte. The device can also contain several solid phase zones which are appropriate for an analyte and different measurement ranges of this analyte. The device contains all reactants and reagents in a dehydrated form.

DESCRIPTION OF PREFERRED EMBODIMENTS

Figure 1:
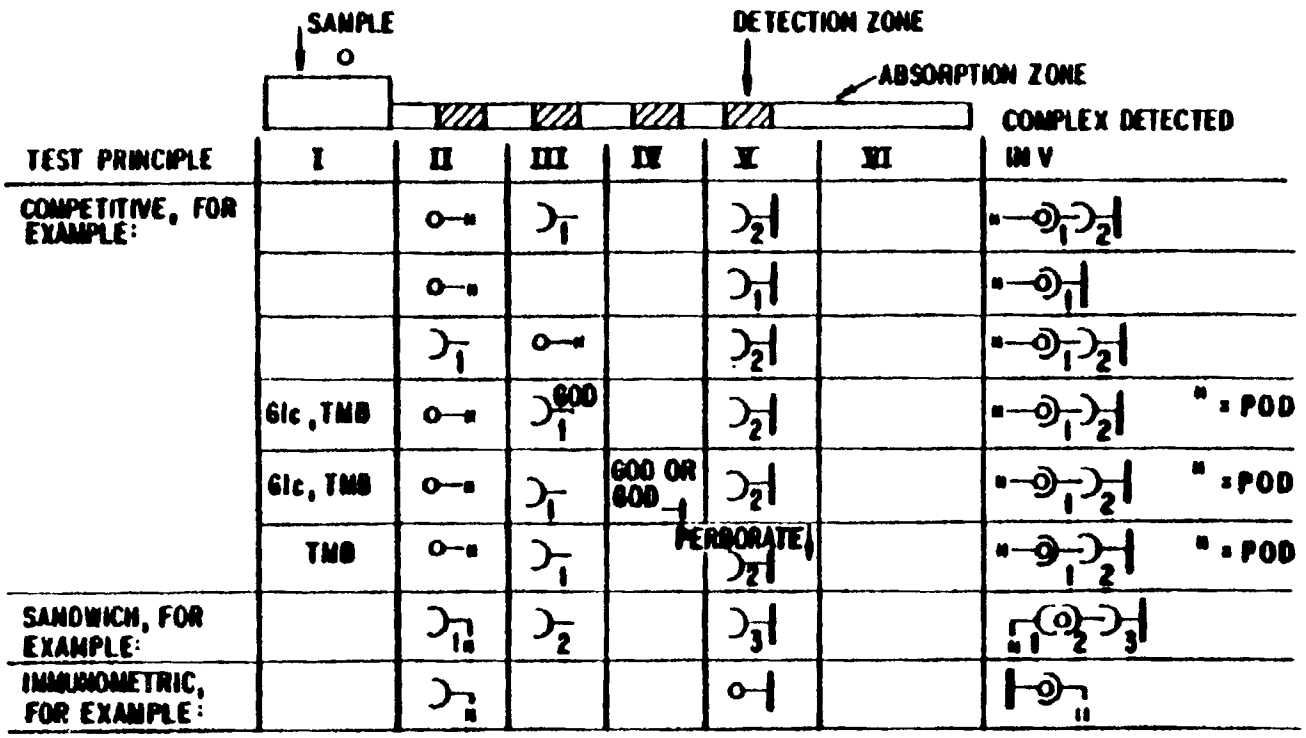
FIG. 1 is a summary table illustrating test assemblies according to certain preferred embodiments of the present invention.

The sheet-like diagnostic device comprises one or several strips, arranged behind one another, of material which have a capacity for absorbing aqueous solutions. The strips are fixed on a solid support. They contain the reagent components required for the particular diagnostic agent and thus become functional sectors or functional regions. The functional sector situated at one end of the strip-shaped device (solvent application zone) is brought into contact with the analyte solution by being dipped into the latter or by the application of the latter. The solution migrates through all the functional regions. The absorptive capacity of the supporting materials of which the strips are composed causes a flow of liquid which stops at the other end of the strip-shaped device. The analyte can also be applied in the middle region of the device, and a flow of liquid from one end of the device to the other can then be induced.

The sample does not have to be applied directly to the chromatographing section of the device. It can also be applied to an absorptive material which is situated on the device and has the function of removing blood cells from the sample. After being filtered the sample then reaches the device. In the course of this filtration process the addition of reagents can be effected at the same time by dissolving the latter out of components present in the filter in a dry state. Interfering factors can be eliminated from the solution by means of such components. Thus, for instance, the ascorbic acid present in a sample, which interferes in the use of oxidases and peroxidases as labelling agents, can be rendered harmless by means of a suitable oxidizing agent. Furthermore, the filter can also have the function of an adsorbent which removes interfering factors from the sample by adsorption. The filtration, adsorption and reagent admixing function for conditioning the sample for the test can also be taken over by the mobile phase application zone or a zone situated behind the latter.

The distribution of the solvent in the individual functional regions depends on the adsorptive capacity and the dimensions of the materials used.

The solvent application zone can have the function of a volume metering element, as described in German Patent Nos. 3,043,608 and 2,232,760, and U.S. Pat. Nos. 3,464,560, 3,600,306, 3,667,607, 3,902,847, 4,144,306 and 4,258,001. It can contain, in dry form, the various reagents required for the function of the test element. The solvent application zone can be a piece of fabric paper which is located at one end of the test element and which becomes completely saturated with a definite volume of liquid merely by being dipped into a solution, for example a solution of the sample, or by being briefly flushed with tap water, and then releases the liquid to the succeeding zones more slowly and in a controlled manner. The solvent application zone has dimensions such that it takes up sufficient liquid to permit the latter to migrate to the other end of the device, the end of the absorption zone.

Between the solvent application zone and the absorption zone there are located the functional regions in which are contained reaction components for the performance of the test and in which all the reaction stages of the performance of the test take place. Part of the reaction components for the performance of the test can also be housed in the sample application zone. The absorption zone has the function of absorbing excess and freely mobile reagent components and reaction products of the single-producing system.

The absorbent supporting materials in the form of one or more strips, as constituents of the various functional regions, can, according to choice, be composed of cellulose, of chemical derivatives of cellulose or of plastics having a porous or fibrous structure and adequately hydrophillic properties, or of particles such as cellulose or silica gel embedded in a synthetic membrane, and also of natural products which are hydrophilic but have been rendered insoluble in water. A combination of strips composed of different materials can be used. Suitable absorbent materials are selected on the basis of the requirements set for the particular diagnostic device.

Reactants with immunological binding properties such as antigens, haptens or antibodies are incorporated in various embodiments of the device. In the event that glycoproteins or oligosaccharides which attach themselves to lectins are to be detected, one reactant having biological affinity can be the specific lectin, while the second reactant having immunological affinity can be an antibody which is directed against a point of attachment on the analyte other than that of the lectin. In the event that microbial active compounds are to be detected. One combination partner can be the receptor substance for the active compound, while the second combination partner can be an antibody which is directed against another point of attachment on the active compound.

One combination partner having biological affinity becomes attached during the progress of the reaction, or has already been attached to the supporting material in the functional region designed for the detection of the analyte (solid phase zone). It is also called the solid phase combination partner. The other combination partner(s) are present in the supporting materials. They are provided with a labelling.

Amongst the various known possibilities of labelling, enzyme labelling is preferred. It requires chromogenic substrate systems or substrate systems which produce fluorescence or chemiluminescence. Chemiluminescence labelling represent a further example of a labelling which is only measured after the addition of a reagent. It is possible to measure either the chemiluminescence itself or a fluorescence excited by the latter. In most cases fluorescence labelling is measured without the addition of a reagent being required. However, as in the use of certain rare earth chelates, it can also be desirable to produce the fluorophore to be measured only as the result of adding a reagent, or to add a second fluorophore which becomes excited by the first or which excites the first fluorophore. The fluorescence can be measured at one point, as a function of time or as fluorescence polarization.

A reagent required for detection can be induced to react with the immune complex to be detected in various ways, after the separation stage. Part of the signal-producing system can be located in the sold phase zone. After the solid phase has been adequately washed, a reagent required to detect the labelling can be released at a retarded rate in various embodiments in the heterogeneous immunoassay with detection in the bound phase. The following are possible examples:

The application of reagents by means of a stream of liquid arranged parallel to the main stream of liquid, but flowing more slowly and starting from the mobile phase reservoir and entering in front of the zone containing the labelled component. The parallel stream of liquid can be controlled by using an absorbent medium which chromatographs more slowly, for example a paper which chromatographs suitably slowly or a paper which is integrated in places with "components temporarily blocking the way", such as, for example, polymers which impart a high viscosity on passing into solution (for example polyvinyl alcohols or dextrans).

After the solid phase has been adequately washed (=completion of chromatography), the application of reagents can be effected by pressing down an element which is a solid constituent of the test element. The "pressing down" can be effected mechanically or by removing distance pieces by the action of a stream of liquid. For example, the mechanical pressing down of an element containing the reagents can be effected by pressing down a flap or a piece of paper supported by distance pieces. The lowering of an element containing the reagents by the action of the stream of liquid can be effected, for example, by laminating over one another the solid phase, a water-soluble polymer and the reagent carrier (for example a suitably impregnated piece of paper).

A retarded introduction of reagents into the liquid stream can be effected using a microencapsulated reagent which only emerges from the encapsulation after the solid phase has been adequately washed, or by coating the reagent adhering in the matrix with components which dissolve slowly.

One possible means presented for the special case of enzyme labelling is as follows: when a peroxidase labelling is used, a glucose oxidase zone can be placed in front of the solid phase zone. Glucose and also the chromogen are then incorporated into the liquid stream, which can result in color formation behind the glucose oxidase. Appreciable color formation is only observed if, at an appropriately high concentration of peroxidase, sufficient $H_2O_2$ is formed by the oxidase. This formation of the peroxide sets in slowly, reaches an optimum concentration and finally reaches a high concentration which results in inhibition of the enzyme and thus automatic cessation of the color formation. This coloration can be moderated if an $H_2O$-acceptor, for example a thioether as a mild reducing agent, or the enzyme catalase is incorporated in the oxidase zone or in front of the latter.

In this example a reagent for detecting the labelling is produced by a delay circuit, making use of an enzyme. The color formation in the solid phase zone only begins after this zone has been adequately washed free from nonspecifically bound labelling by the stream of liquid.

There are several possible means of preparing the solid phase zone. The components fixed there can be attached by chemical covalent bonds or adsorptively to an absorptive support which is a part of the test element. These components can also be attached to a dispersion of particles which remain fixed at the place of application after they have been applied to an absorbent support. For example, suspensions of cells carrying specific receptors on their surface, such as, for instance, Staphylococcus aureus Cowan I cells, or latex particles carrying combination partners of biological affinity attached to their surface, are suitable for being fixed in a paper matrix. The components of the test strip which are attached to pipettable supports and also the unattached components of the device can be dried onto the absorbent matrix of the element by air drying freezedrying stages are not absolutely necessary.

A few test performance will be illustrated as examples of embodiments which can be regarded as independent of the labelling used. For the sake of simplicity, they are only described for the detection of a single analyte by means of the diagnostic device.

The following two embodiments, which conform to the principle of competitive immunoassay, will be described for the case where the analyte has only a single combination point of biological affinity or only one combination point of biological affinity out of several is utilized:

The solid phase combination partner is attached by covalent bonds or adsorptively to the supporting material of the solid phase functional region. The solution of analyte renders mobile a predetermined amount of labelled analyte contained in the diagnostic agent. The two components migrate into the functional sector containing the solid phase combination partner and compete for combination with the solid phase combination partner. If the proportion of analyte is high compared with the labelled analyte, little labelled analyte will be attached. If it is low, a great deal of labelled analyte will be attached.

The solid phase combination partner is housed as an unattached component in a functional region in front of the solid phase functional region. The oncoming front of solvent transports it into the solid phase functional region, where it becomes attached. This solid phase attachment is produced by combination systems of biological affinity which are independent of the combination system of the analyte. A combination partner which is conjugated with biotin attaches itself to avidin attached to the support. An immunoglobulin, such as IgG, as a combination partner, is fixed via its Fc component to support-attached protein A of S. aureus, or is attached by solid phase antibody of another species, non idiotypically directed to said immunoglobulin.

As previously described, the analyte and the labelled analyte compete, as constituents of the diagnostic agent, for the attachments to the solid phase combination partner during the processing period. This competition reaction takes place partly with the dissolved solid phase combination partner and partly with the solid phase combination partner which has already been attached to the solid phase.

If two combination points of differing specificity are present in an analyte, several embodiments, conforming to the principle of sandwich immunoassay, of the diagnostic agent are conceivable. Two of these will also be illustrated below.

If the solid phase combination partner is attached by covalent bonds or adsorptively to the supporting material of the solid phase functional region, the analyte forms, with the labelled combination partner, a binary complex which migrates together with the solvent into the solid phase functional region and reacts there with the solid phase combination partner, with the formation of a ternary complex, attached to the solid phase, which can be detected via the labelling of the first combination partner. The excess labelled combination partner is removed by the solvent into the subsequent functional region, the absorption zone.

If the solid phase combination partner is present in a non-attached form in the diagnostic agent and is rendered mobile by the solvent, the two reactions of the analyte of biological affinity are housed in the functional regions in such a way that the analyte reacts simultaneously or successively with both reactants and the resulting tertiary complex then migrates into the solid phase functional region, where, as already described above, it becomes attached to the solid phase via a second system of biological affinity which is independent of that of the analyte.

Figure 2:
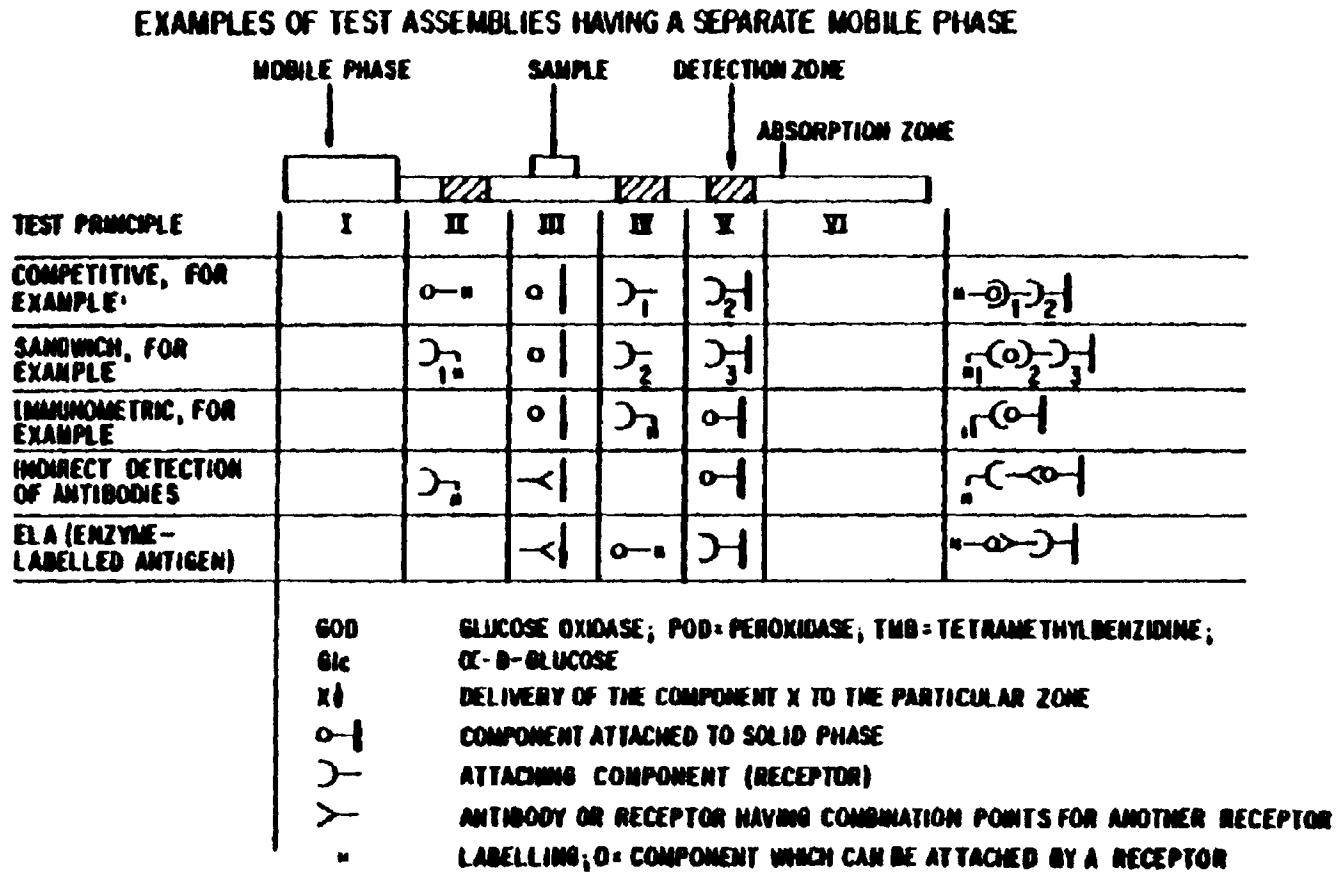
FIG. 2 is a summary table illustrating test assemblies according to certain preferred embodiments of the present invention.

In order to illustrate the embodiments described above and further embodiments which conform to the immunometric test principle, the principle of indirect, antibody detection or the ELA (enzyme-labelled-antigen) principle of immunoassay, FIGS. 1 and 2 illustrate in an exemplary manner the distribution of the components of the agent in the functional regions and, after the performance of the reaction, the composition of the solid phase complex, the amount of which is a measure of the concentration of analytes in the sample.

It has been found that a completely integrated test strip operating in accordance with the principle of heterogeneous immunoassay by means of solid phase detection is not only feasible in principle, but can, in addition, also be evaluated within a period of less than one hour, the quantification and the sensitivity of conventional RIAs or ELISAs being achieved. The detection of trace components in the range of $10^{-12}$ mol/liter has been made possible at reaction times of less than 30 minutes, at room temperature, the amounts of sample required being $10^{-16}$ mol, corresponding, for example, to approx. 1 pg. The arrangements described also enable tests of lower sensitivity requirements to be carried out, however. Standard curves over two to three decades were obtained when evaluation was carried out with the Sanoquell reflectometer (made by Quelle). The chromatography time for the test element, including complete color development, is not more than 16 minutes. Evaluation can also be carried out visually. With HCG as analyte, the start of the range of determination in an example using a glucose oxidase attached to a solid phase and a peroxidase labelling was 0.3 ng/ml (corresponding to 3 U/liter).

In the example following, the application of the principle of the competitive double antibody test is presented as a concrete embodiment. In this test configuration, four components have to be reacted successively for the determination reaction and the separation stage, the reaction times and the concentrations of the reactant being critical values. The example is not to be regarded as limiting in any way, but merely serves to illustrate the subject of the invention further.

EXAMPLE

Completely integrated enzyme-immunochemical device for the detection of HCG by means of a built-in chromogen substrate system.

1.1 Reagents

1.1.1. HCG-peroxidase conjugate

HCG having a specific activity of approx. 3000 U/mg was obtained from Organon. Peroxidase from horseradish was obtained from Boehringer Mannheim (catalog no. 413,470). The hetero-bifunctional reagent N-γ-maleimidobutyryloxysuccinimide (GMBS) was obtained from Behring Diagnostics and was reacted with the HCG as described by Tranimori et al., 1983, in J.Imm. Meth. 62, 123–131. 2-iminothiolane hydrochloride (Sigma, catalog no. I 6256) was reacted with peroxidase as described by King et al., 1978, in Biochemistry 17, 1499–1506. A conjugate was prepared from the GMBS-HCG and the iminothiolane-peroxidase as described by Tanimori et al. The crude conjugate was purified by gel chromatography over Ultrogel ACA 44 (LKB). The fraction in which about 1–2 peroxidase molecules were coupled per HCG molecule was used for the test. The conjugate was diluted with Enzygnost IgE incubation medium made by Behringwerke, order no. OS D, designated briefly as incubation medium in the following text.

1.1.2. Antibodies

Antibodies against HCG were obtained by immunizating rabbits, and antibodies against rabbit-IgG were obtained by immunizing goats. The IgG fractions were isolated from serum by ammonium sulfate precipitation and anion exchange chromatography, and were purified further by immunadsorption. The methods used are described in the book "Immunologische Arbeitsmethoden" (Immunological working methods), Helmut Friemel, Editor, 1984, Gustav Fisher Verlag, Stuttgart. The anti-HCG antibody was finally diluted in the conjugate dilution biffer indicated above.

1.1.3 Glucose oxidase

Glucose oxidase from Aspergillus niger was obtained as a solution containing 300 U/mg (Serva, catalog No. 22,737). The glucose oxidase was finally diluted with incubation medium.

1.1.4 Glucose and Tetramethylbenzidine

α-D-glucose and tetramethylbenzidine hydrochloride were obtained from Serva, catalog no. 22,720 and 35,926, respectively.

1.2 Preparation of the Device

The sheet-like functional regions were prepared as follows:

The mobile phase application zone was prepared by cutting, to dimensions of 20×6 mm, a fabric sponge cloth made by Kalle; this is a synthetic sponge of regenerated cellulose which has been compressed in a dry state. It was impregnated with a solution of 50 mg of glucose and 0.75 mg of tetramethylbenzidine hydrochloride per ml of water, and was dried in a stream of air.

The conjugate, the anti-HCG antibody and glucose oxidase (5 μl of each at 25 μl/ml, 100 μl/ml and 0.1 mg/ml, respectively) were applied behind one another, at uniform distance, to a 45×5 mm piece of MN no. 1 paper (Macherey & Nagel), and were dried in the air.

A piece measuring 5×5 mm of Schleicher & Schull No. 597 paper was coated in a covalent manner with anti-rabbit IgG-antibody as the solid phase zone. This was effected by coupling the antibody with the paper, which had been activated with cyanogen bromide, as described by Clarke et al., 1979, Meth.Enzymology, volume 68, 441–442.

A 20×5 mm piece of Schleicher & Schüll No. 2688/8 paper was used as the absorption zone.

The four pieces of paper, with a 0.5–1 mm overlap behind one another, were fixed on a plastic ribbon by means of double-sided adhesive tape (Tesaband made by Beiersdorf), so that a test strip 5 mm wide was formed.

1.3 Performance of the Test

The test was carried out in each case by applying 200 μl of an HCG dilution in incubation medium to the fabric.

1.4 Results

The chromatographic development of the test element and the self-actuating color development were complete after 15 minutes at room temperature, and evaluation could be carried out either visually or by means of a reflectometer.

The following values were obtained when evaluating the solid phase zone (No. 597 paper) with the Sanoquell blood glucose evaluation apparatus made by Quelle:

| HCG concentration (U/liter) | Measured values (mg of glucose per dl of blood) |
|---|---|
| 0.3 | 107 |
| 3 | 117 |
| 30 | 95 |
| 300 | 70 |
| 3000 | 0 |

The following values were obtained with the same test strips using the Rapimat urine test strip evaluation apparatus made by Behringwerke:

| HCG concentration (U/liter) | Measured values (BIT) |
|---|---|
| 0.3 | 76 |
| 3 | 76 |
| 30 | 94 |
| 300 | 119 |
| 3000 | 135 |

The test strip assembly shown here can also be achieved if the glucose oxidase and the anti-HCG antibody are located in the same zone. The test strip, which is correspondingly shorter, then renders the result after approx. 10 minutes.

We claim:

[1. An analytical device for the detection or determination of a component in a fluid wherein said component is an analyte with bioaffinity binding properties, comprising a layer of a plurality of substantially planar zones adjacent one another and in absorbent contact with one another, said layer including:

a mobile phase application zone (MPAZ), an intermediate zone (IZ) and an adsorption zone (AZ), liquid being capable of moving by adsorption from said MPAZ through said IZ to said AZ, and wherein said IZ further comprises a solid phase zone (SPZ) having at least one unlabelled reactant, capable of interactions of biological affinity with at least one analyte;

at least one unattached, labelled reactant (conjugate), capable of interactions of biological affinity with said at least one analyte, disposed in an area between the MPAZ and the SPZ; and an analyte application zone diaposed at said MPAZ or in between said MPAZ and said AZ, wherein after application of said at least one analyte, said at least one analyte is reacted with said reactants in said layer and is detected in said layer.]

[2. A device as claimed in claim 1, wherein the MPAZ has the function of a volume metering element and releases to the subsequent zones at least sufficient liquid for the liquid, controlled by capillary forces, to reach the end of the AZ.]

[3. A device as claimed in claim 1, wherein the MPAZ is a plastic sponge or a particular layer which is composed of hydrophilic polymers and which is capable of containing chemicals, buffer substances or other substances required for certain tests.]

[4. A device as claimed in claim 1, wherein the analyte application zone retains blood cells.]

[5. A device as claimed in claim 1, wherein all or some of the reagents required for the detection of the labelling are present in one or more of substantially planar zones of the device.]

[6. A device as claimed in claim 1, wherein said at least one unlabelled reactant is fixed to said SPZ by means of covalent bonds.]

[7. A device as claimed in claim 1, wherein said at least one unlabelled reactant is fixed to said SPZ by means of absorption.]

[8. A device as claimed in claim 1, wherein said at least one unlabelled reactant is fixed to said SPZ by means of an interaction of biological affinity.]

[9. A device as claimed in claim 1, further including a plurality of solid phase zones (SPZs) for the detection of a plurality of analytes, said analytes including at least one attachment point of biological affinity, each of said SPZs being adjacent one another in said layer and each of said SPZs including said unlabelled reactants fixed thereto, said unlabelled reactants of each SPZ being specific for a specific analyte to be detected in each of said SPZs.]

[10. A device as claimed 1, wherein said layer includes a chromotographing section in at least a portion of said substantially planar zones, and further including a sample application zone laminated onto at least a portion of said chomatographing section and in adsorptive contact therewith.]

[11. A device as claimed in claim 1, wherein said layer includes a chromotographing section in at least a portion of said substantially planar zones, and further including a reagent zone laminated onto at least a portion of said chromotographing section and in adsorptive contact therewith, wherein at least some of the reagents required for the detection of the labelling are present in said reagent zone.]

[12. A process for the detection or determination of a component in a fluid wherein said component is an analyte with bioaffinity binding properties by rehydrating or solving reactants and reagents by the fluid containing the analyte or by an additional fluid, said reactants and reagents being present in a dehydrated state in an analytical device for the detection or determination of a component in a fluid wherein said component is an analyte with bioaffinity binding properties, comprising a layer of a plurality of substantially planar zones adjacent one another and in absorbent contact with one another, said layer including:

a mobile phase application none (MPAZ), an intermediate zone (IZ) and an adsorption zone (AZ), liquid being capable of moving by adsorption from said MPAZ through said IZ to said AZ, and wherein said IZ further comprises a solid phase zone (SPZ) having at least one unlabelled reactant, capable of interactions of biological affinity with at least one analyte;

at least one unattached, labelled reactant (conjugate), capable of interactions of biological affinity with said at least one analyte, disposed in an area between the MPAZ and the SPZ; and an analyte application zone disposed at said MPA or in between said MPAZ and said AZ, said process comprising:

applying a sample to said analyte application zone, reacting the at least one analyte in the sample in said layer and detecting said at least one analyte in said layer.]

[13. The process as claimed in claim 12, wherein, after the liquid sample containing the analyte has been fed to the MPAZ or other the sample has been fed to a sample application zone and a mobile phase has been fed to the MPAZ, the liquid reaches the end of the AZ, under the control of capillary forces, and reactions between reactants contained in the device and the analyte are thereby set in operation, and, after the labelled reactants which are not attached to the solid phase have been removed chromatographically, the amount of the labelling in the solid phase zone, which is a measure of the analyte concentration in the sample, is determined.]

[14. The process as claimed in claim 12, wherein the reactions taking place in the device are based on the principals of at least one of immunological detection reactions, competitive immunometric or sandwich immunoassay, indirect antibody detection by means of a labelled antibody and antibody detection by means of a labelled antigen.]

[15. The process as claimed in claim 12, wherein said detecting includes using a fluorophore as a labelling agent which is detected or measured directly or is detected or measured after the addition of a reagent present in the device, or a fluorophor which is detected or measured directly or after the addition of a further reagent is formed from the labelling agent by the addition of a reagent present in the device.]

[16. The process as in claim 12, wherein said detecting includes using a compound which can be excited to give chemiluminescence as a labelling agent, the chemiluminescence being detectable or measurable after the addition of a reagent present in the device.]

[17. The process as claimed in claim 12, wherein said detecting includes using an enzyme as a labelling agent, the activity of which is determined with the aid of a reagent present in the device.]

[18. An analytical device for the detection or determination of a component in a fluid wherein said component is an analyte with bioaffinity binding properties, comprising a layer of a plurality of substantially planar zones adjacent one another and in absorbant contact with one another, said layer including:

a mobile phase application zone (MPAZ), an intermediate zone (IZ) and an adsorption zone (AZ), liquid being capable of moving by adsorption from said MPAZ through said IZ to said AZ, and wherein said IZ further comprises a solid phase zone (SPZ) capable of having at least one unlabelled reactant fixed thereto which is capable of interactions of bioaffinity with at least one analyte, during analysis said at least one unlabelled reactant being fixed to at least one second reactant which is fixed to said solid phase zone;

at least one unattached labelled reactant (conjugate), capable of interactions of biological affinity with said at least one analyte, disposed in an area between said MPAZ and said SPZ; and an analyte application zone disposed at said MPAZ or in between said MPAZ and said AZ, wherein after application of said at least one analyte, said at least one analyte is reacted with said reactants in said layer and is detected in said layer.]

[19. A device as claimed in claim 18, wherein said at least one second reactant is fixed to said SPZ by means of covalent bonds.]

[20. A device as claimed in claim 18, wherein said at least one second reactant is fixed to said SPZ by means of adsorption.]

[21. A device as claimed in claim 18, wherein said at least one second reactant is fixed to said SPZ by means of an interaction of biological affinity.]

[22. A device as claimed in claim 18, further including a plurality of solid phase zones (SPZs) for the detection of a plurality of analytes, said analytes including at least one attachment point of biological affinity, each of said SPZs being adjacent one another in said layer and each of said SPZs including said unlabelled reactants fixed thereto, said unlabelled reactants of each SPZ being specific for a specific analyte to be detected in each of said SPZs.]

[23. A device as claimed in claim 18, wherein the MPAZ has the function of a volume metering element and releases to the subsequent zones at least sufficient liquid for the liquid controlled by capillary forces, to reach the end of the AZ.]

[24. A device as claimed in claim 18, wherein the MPAZ is a plastic sponge or a particulate layer which is composed of hydrophilic polymers and which is capable of containing chemicals, buffer substances or other substances required for certain tests.]

[25. A device as claimed in claim 18, wherein the analyte application zone retains blood cells.]

[26. A device as claimed in claim 18, wherein said layer includes a chromotographing section in at least a portion of said substantially planar zones; and further including a sample application zone laminated onto at least a portion of said chromatographing section and in adsorptive contact therewith.]

[27. A device as claimed in claim 18, wherein all or some of the reagents required for the detection of the labelling are present in one or more of the substantially planar zones of the device.]

[28. A device as claimed in claim 18, wherein said layer includes a chromotographing section in at least a portion of said substantially planar zones, and further including a reagent zone laminated onto at least a portion of said chromotographing section and in absorptive contact therewith, wherein at least some of the reagents required for the detection of the labelling are present in said reagent zone.]

[29. A process for the detection or determination of a component in a fluid as an analyte with bioaffinity binding properties by rehydrating or solvating reactants and reagents by the fluid containing the analyte or by an additional fluid, said reactants and reagents being present in a dehydrated state in an analytical device for the detection or determination of the analyte, said device including a layer of a plurality of substantially planar zones adjacent one another and in absorbent contact with one another, said layer including:

a mobile phase application zone (MPAZ), an intermediate zone (IZ) and an adsorption zone (AZ), liquid being capable of moving by adsorption from said MPAZ through said IZ to said AZ;

a solid phase zone (SPZ) in said IZ capable of having at least one unlabelled reactant fixed thereto which is capable of interactions of bioaffinity with at least one analyte, during analysis said at least one unlabelled reactant being fixed to at least one second reactant which is fixed to said solid phase zone;

at least one unattached labelled reactant (conjugate), capable of interactions of biological affinity with said at least one analyte, disposed in a zone between the MPAZ and the SPZ; and an analyte application zone disposed at said MPAZ or in between said MPAZ and said AZ;

said processing comprising:

applying a sample to said analyte application zone, reacting the at least one analyte in the sample in said layer and detecting said at least one analyte in said layer.]

[30. The process as claimed in claim 29, wherein, after the liquid sample containing the analyte has been fed to the MPAZ or after the sample has been fed to a sample application zone and a mobile phase has been fed to the MPAZ, the liquid reaches the end of the AZ, under the control of capillary forces, and reactions between reactants contained in the device and the analyte are thereby set in operation, and, after the labelled reactants which are not attached to the solid phase have been removed chromatographically, the amount of the labelling in the solid phase zone, which is a measure of the analyte concentration in the sample, is determined.]

[31. The process as claimed in claim 29, wherein the reactions taking place in the device are based on the principals of at least one of immunological detection reactions, competitive immunometric or sandwich immunoassay, indirect antibody detection by means of a labelled antibody and antibody detection by means of a labelled antigen.]

[32. The process as claimed in claim 29, wherein said detecting includes using a fluorophor as a labelling agent which is detected or measured directly or is detected or measured after the addition of a reagent present in the device, or a fluorophor which is detected or measured directly or after the addition of a further reagent is formed from the labelling agent by the addition of a reagent present in the device.]

[33. The process as in claim 29, wherein said detecting includes using a compound which can be excited to give chemiluminescence as a labelling agent, the chemiluminescence being detectable or measurable after the addition of a reagent present in the device.]

[34. The process as claimed in claim 29, wherein said detecting includes using an enzyme as a labelling agent, the activity of which is determined with the aid of a reagent present in the device.]

*35. An analytical device for the detection or determination of a component in a fluid wherein said component is an*

*analyte with bioaffinity binding properties, comprising a layer of a plurality of substantially planar zones adjacent one another and in absorbent contact with one another, said layer including:*

*a mobile phase application zone (MPAZ), an intermediate zone (IZ), and an adsorption zone (AZ), liquid being capable of moving by adsorption from said MPAZ through said IZ to said AZ, and wherein said IZ comprises a solid phase zone (SPZ) having at least one unlabelled reactant, capable of interactions of biological affinity with an analyte;*

*at least one unattached, labeled reactant (conjugate) capable of interactions of biological affinity with said analyte disposed in an area between the MPAZ and the SPZ; and*

*an analyte application zone disclosed at said MPAZ or in between said MPAZ and said AZ, and*

*wherein all reactants necessary for the detection or determination are present in a dehydrated form in the device, and*

*wherein said MPAZ has dimensions to contain sufficient fluid to permit the fluid to migrate to the AZ, and*

*wherein said layer of substantially planar zones contains at least two sheet-like strips made from different materials, and*

*wherein after application of said analyte, said analyte is reacted with said reactants in said layer and is detected in said layer.*

*36. The device of claim 35, wherein the analyte is an antigen and the unlabelled reactant and the labelled reactant are antibodies.*

*37. The device of claim 35, wherein the analyte is an antibody and the unlabelled reactant and the labelled reactant are antigens.*

*38. The device of claim 35, wherein the analyte is an antigen and the unlabelled reactant is an antibody and the labelled reactant is an antigen.*

*39. The device of claim 35, wherein the analyte is an antibody and the unlabelled reactant is an antigen and the labelled reactant is an antibody.*

*40. The device of claim 35, wherein the analyte is a protein and the unlabelled reactant and the labelled reactant are antibodies.*

*41. The device of claim 35, wherein the analyte is hCG and the unlabelled reactant and the labelled reactant are antibodies specific for hCG.*

*42. The device of claim 35, wherein the unattached labelled reactant is labelled directly or indirectly with an enzyme.*

*43. The device of claim 35, wherein the analyte is hCG.*

*44. The analytical device of claim 35, wherein the AZ is an area where excess unattached, labeled reactant is removed from the SPZ.*

*45. The device of claim 35, wherein the analyte is an antigen and the unlabelled reactant is an antigen and the labeled reactant is an antibody.*

*46. An analytical device for the detection of beta-hCG in a fluid sample by means of a sandwich immunoassay comprising a layer of a plurality of substantially planar zones adjacent one another and in absorbent contact with one another, said layer including:*

*a mobile phase application zone (MPAZ), an intermediate zone (IZ) and an adsorption zone (AZ), liquid being capable of moving by adsorption from said MPAZ through said IZ to said AZ, and wherein said IZ further comprises a solid phase zone (SPZ) having at least one unlabelled antibody, capable of an immunological interaction with beta-hCG;*

*at least one unattached labeled antibody (conjugate) capable of an immunological interaction with beta-hCG, disposed in an area between the MPAZ and the SPZ; and*

*an analyte application zone disposed at said MPAZ,*

*wherein the MPAZ has dimensions to contain sufficient fluid to permit the fluid to migrate to the end of the AZ, and*

*wherein said layer of substantially planar zones contains at least two sheet-like strips made from different materials, and*

*wherein after application of said fluid sample, the presence of beta-hCG is detected visually in the SPZ.*

*47. The analytical device of claim 46, wherein the unattached labeled antibody is labeled with an enzyme.*

*48. The analytical device of claim 46, wherein the AZ is an area where excess unattached, labeled antibody is removed from the SPZ.*

* * * * *

UNITED STATES PATENT AND TRADEMARK OFFICE

CERTIFICATE OF CORRECTION

PATENT NO. : RE 38,688 E
DATED : January 18, 2005
INVENTOR(S) : Heinz-Jürgen Friesen et al.

It is certified that error appears in the above-identified patent and that said Letters Patent is hereby corrected as shown below:

Column 13,
Line 16, change "disclosed" to -- disposed --.

Signed and Sealed this

Twenty-fourth Day of May, 2005

JON W. DUDAS
*Director of the United States Patent and Trademark Office*